(12) United States Patent
Akingba

(10) Patent No.: US 10,836,601 B2
(45) Date of Patent: Nov. 17, 2020

(54) GUIDEWIRE MANAGEMENT APPARATUS AND METHOD

(71) Applicant: Ajibola George Akingba, Birmingham, MI (US)

(72) Inventor: Ajibola George Akingba, Birmingham, MI (US)

(*) Notice: Subject to any disclaimer, the term of this patent is extended or adjusted under 35 U.S.C. 154(b) by 188 days.

(21) Appl. No.: 16/052,933

(22) Filed: Aug. 2, 2018

(65) Prior Publication Data

US 2019/0276268 A1 Sep. 12, 2019

Related U.S. Application Data

(60) Provisional application No. 62/639,573, filed on Mar. 7, 2018.

(51) Int. Cl.
| | | |
|---|---|---|
| *B65H 75/30* | (2006.01) | |
| *B65H 75/44* | (2006.01) | |
| *A61M 25/00* | (2006.01) | |
| *A61M 25/01* | (2006.01) | |
| *A61M 25/09* | (2006.01) | |

(52) U.S. Cl.
CPC ....... *B65H 75/4402* (2013.01); *A61M 25/002* (2013.01); *A61M 25/0113* (2013.01); *A61M 25/09041* (2013.01); *B65H 75/30* (2013.01); *B65H 75/4478* (2013.01)

(58) Field of Classification Search
CPC ................ B65H 75/30; B65H 75/4402; B65H 75/4478; A61M 25/002; A61M 25/0113; A61M 25/09041
See application file for complete search history.

(56) References Cited

U.S. PATENT DOCUMENTS 3,561,445 A * 2/1971 Katerndahl ........ A61M 25/0113
604/159
3,964,490 A * 6/1976 Nelms ...................... A61N 1/02
607/2

(Continued)

FOREIGN PATENT DOCUMENTS

WO WO9711736 A1 4/1997
WO WO03061729 A2 7/2003

OTHER PUBLICATIONS

The European Search Report and Written Opinion for EP 19161366, dated Sep. 9, 2019, 12 pages.

*Primary Examiner* — Sang K Kim
(74) *Attorney, Agent, or Firm* — Brett A. Schenck

(57) ABSTRACT

An apparatus for storing and directing a guidewire used to guide an instrument is provided and includes a spool. The spool receives the guidewire and a spool wire. Rotation of the spool in a first direction retracts the guidewire and the spool wire around the spool. The apparatus also includes a wire connector that operatively couples the spool wire and the guidewire together. The apparatus further includes a housing that houses the spool. The housing includes first and second apertures. The first aperture is sized to prevent the wire connector from passing through the first aperture but allow the guidewire and the spool wire to pass through the first aperture. The second aperture is sized to allow the wire connector and the guidewire and the spool wire to pass through the second aperture. The first and second apertures merge together such that the guidewire and the spool wire may move between the first and second apertures.

17 Claims, 14 Drawing Sheets

(56) References Cited

U.S. PATENT DOCUMENTS

| | | | |
|---|---|---|---|
| 4,875,481 | A | 10/1989 | Higgins |
| 5,827,202 | A | 10/1998 | Miraki et al. |
| 5,843,002 | A | 12/1998 | Pecor et al. |
| 6,086,008 | A | 7/2000 | Gray et al. |
| 6,231,564 | B1 | 5/2001 | Gambale |
| 6,327,507 | B1 * | 12/2001 | Buchan ............ A61N 1/02 191/12.4 |
| 7,344,515 | B2 | 3/2008 | Coyle |
| 7,544,170 | B2 | 6/2009 | Williams et al. |
| 8,095,223 | B2 | 1/2012 | Cleary et al. |
| 8,348,034 | B2 * | 1/2013 | Fila ............ A61B 18/08 191/12.2 R |
| 8,523,808 | B2 | 9/2013 | Selkee |
| 8,702,025 | B2 * | 4/2014 | Kish ............ B65H 75/4434 242/378.1 |
| 9,623,207 | B2 | 4/2017 | Akingba et al. |
| 2004/0087966 | A1 | 5/2004 | Mcdevitt |
| 2005/0184187 | A1 | 8/2005 | Ullman et al. |
| 2006/0064058 | A1 | 3/2006 | Coyle |

\* cited by examiner

GUIDEWIRE MANAGEMENT APPARATUS AND METHOD

FIELD

This application relates to an apparatus and a method for managing a guidewire used to guide a catheter and catheter-based interventional devices.

BACKGROUND

Interventional and diagnostic procedures require the insertion of an external instrument into a patient's body. Guidewires may be used in catherization and other procedures to aid in inserting and directing the instrument into a desired location.

The use of a guidewire reduces the risk of trauma to the patient by the advancing catheter and enables the catheter to be advanced quickly, thereby reducing the time required for the procedure. When used in complex endovascular procedures, multiple guidewires and multiple guidewire exchanges are often required to accommodate the multiple devices utilized. This makes management of multiple wires and multiple wire exchanges a necessity in order to primarily optimize time, space and reduce mishaps associated with these complex procedures. For example, it takes about 20-30 seconds to replace a wire into its plastic-housing and wire exchanges can be done 15-30 times during a complex endovascular procedure. When the wire is placed in an uncoiled-position, it can take up to 5-10 feet of space (longitudinally), which limits the size of room that these procedures can be performed within.

Also, when the wire is placed in a coiled position, it has inherent potential energy that can cause it to uncoil and get contaminated (and/or damaged) leading to disposal and wastage of wires. Further, it may be costly due to the space required to store the uncoiled guidewire length and the time to exchange guidewires. For example, the cost of a hybrid operating room may be $500 per square foot. A typical or extension table used to lay the wires in an uncoiled fashion, is about 20 to 30 square feet. The cost per minute of operating time in a typical operating room may be about $133 per minute. Generally, in a complex interventional procedure it takes an additional 20 to 30 minutes of wire exchange time, which may cost approximately up to $4000 for this type of procedure. Also, wire contamination resulting in the replacement of wires is somewhat difficult to quantify, but happens enough to warrant a better solution.

Devices for storing and cleaning a guidewire are well known. Conventional guidewire storage devices are generally large, cumbersome bowls or basins with rims inside to keep the guidewire in a saline bath. Often, these storage devices allow for numerous wires to get tangled, making it difficult to find and remove a wire in a timely manner. The awkward nature of using such devices often results in wires falling to the floor or otherwise becoming contaminated.

Hence, there remains a need to make the storage, cleansing, and access of guidewires during medical and surgical procedures more efficient.

SUMMARY

In one aspect of the present invention, an apparatus for storing and directing a guidewire used to guide an instrument is provided. The apparatus includes a spool that receives the guidewire. Rotation of the spool in a first direction retracts the guidewire around the spool. The apparatus also includes a housing that houses the spool. The housing includes a cap that is removably attached to the housing. The apparatus further includes a spool stop member. The spool stop member is provided between the cap and the spool. The spool stop member is configured to brake the spool during rotation of the spool.

In another aspect of the present invention, an apparatus for storing and directing a guidewire used to guide an instrument is provided and includes a spool. The spool receives the guidewire and a spool wire. Rotation of the spool in a first direction retracts the guidewire and the spool wire around the spool. The apparatus also includes a wire connector that operatively couples the spool wire and the guidewire together. The apparatus further includes a housing that houses the spool. The housing includes first and second apertures. The first aperture is sized to prevent the wire connector from passing through the first aperture but allow the guidewire and the spool wire to pass through the first aperture. The second aperture is sized to allow the wire connector and the guidewire and the spool wire to pass through the second aperture. The first and second apertures merge together such that the guidewire and the spool wire may move between the first and second apertures.

In another aspect of the present invention, an apparatus for storing and directing a guidewire used to guide an instrument is provided. The apparatus includes a spool that receives the guidewire. Rotation of the spool in a first direction retracts the guidewire around the spool. The apparatus also includes a brake, wherein the brake may be placed in a first position in which the brake does not prevent the spool from rotating in the first direction. The brake may be placed in a second position in which the brake engages the spool to prevent the spool from rotating in the first direction. The apparatus also includes a brake actuator operatively connected to the brake. Actuation of the brake actuator causes the brake to move from the first position to a second position. The apparatus further includes a brake lock operatively connected to the brake. The brake lock is configured to lock the brake in the second position to prevent the spool from retracting the guidewire without continue actuation of the brake actuator.

Other aspects of the disclosed apparatus and method for managing a guidewire will become apparent from the following detailed description, the accompanying drawings and the appended claims.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

Figure 1:
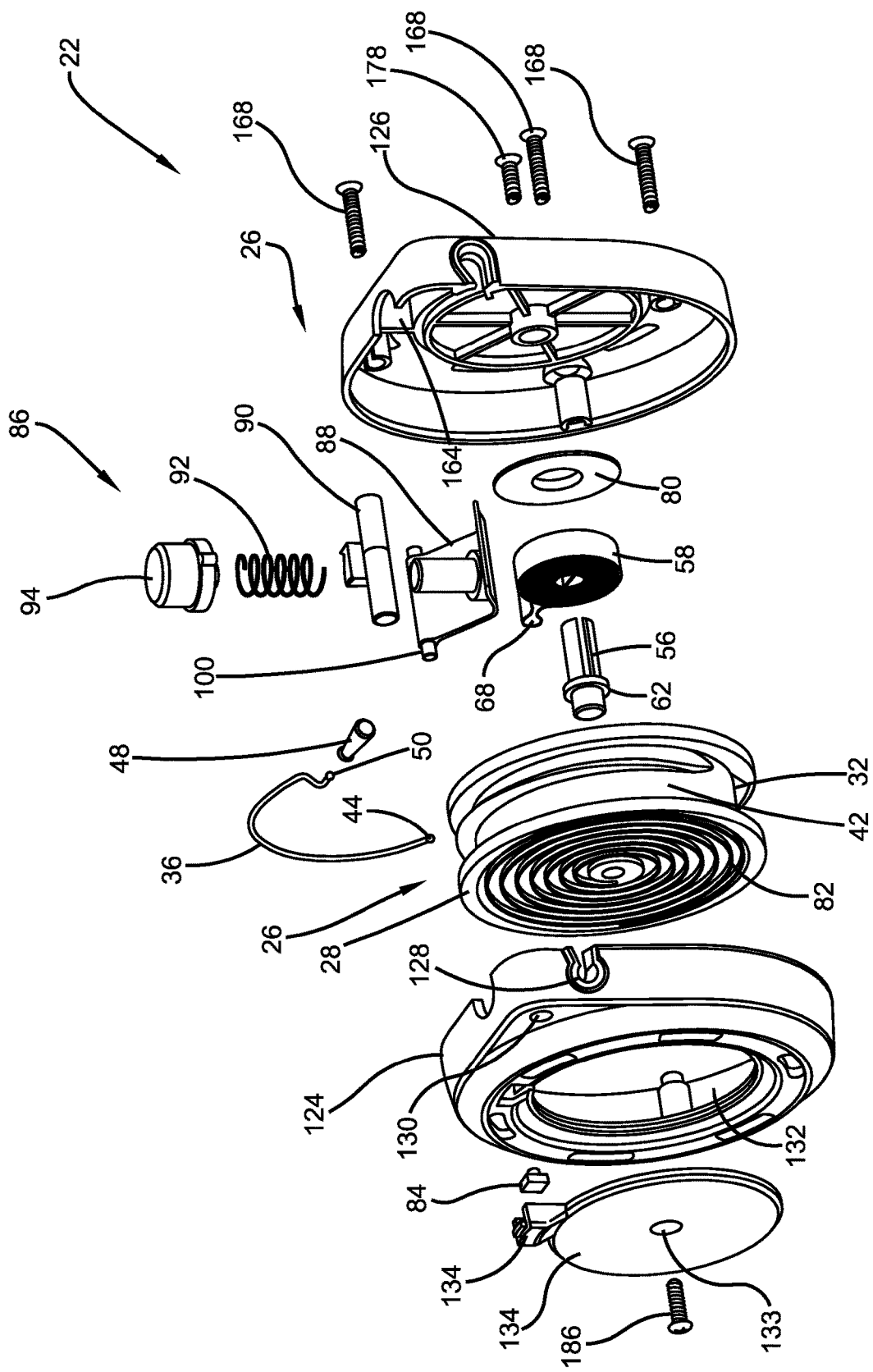
FIG. 1 is an exploded view of the apparatus for managing a guidewire as viewed from the front and right side according to an embodiment of the present invention.

Throughout the present description, the terms "upper", "lower", "top", "bottom", "left", "right", "front", "forward", "rear", and "rearward" shall define directions or orientations with respect to the apparatus for managing the guidewire as illustrated in FIG. 1. It will be understood that the spatially relative terms "upper", "lower", "top", "bottom", "left", "right", "front", "forward", "rear", and "rearward" are intended to encompass different orientations of the apparatus for managing a guidewire in use or operation in addition to the orientation depicted in the figures. For example, if the apparatus in the figures is turned over, elements described as "upper" elements or features would then be "lower" elements or features.

Figure 2:
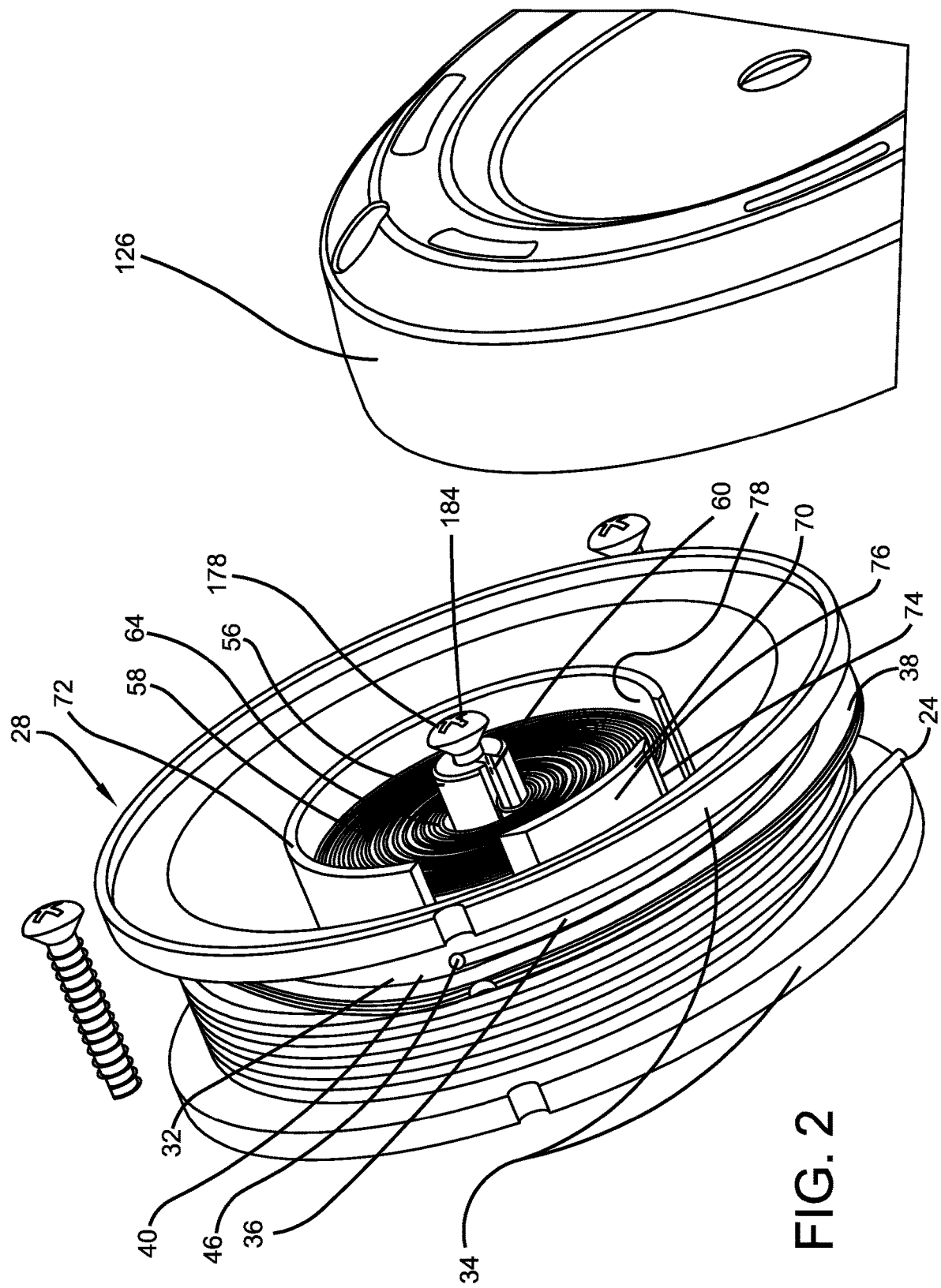
FIG. 2 is an exploded view of a portion of the apparatus of FIG. 1 as view from the rear side.
Figure 6:
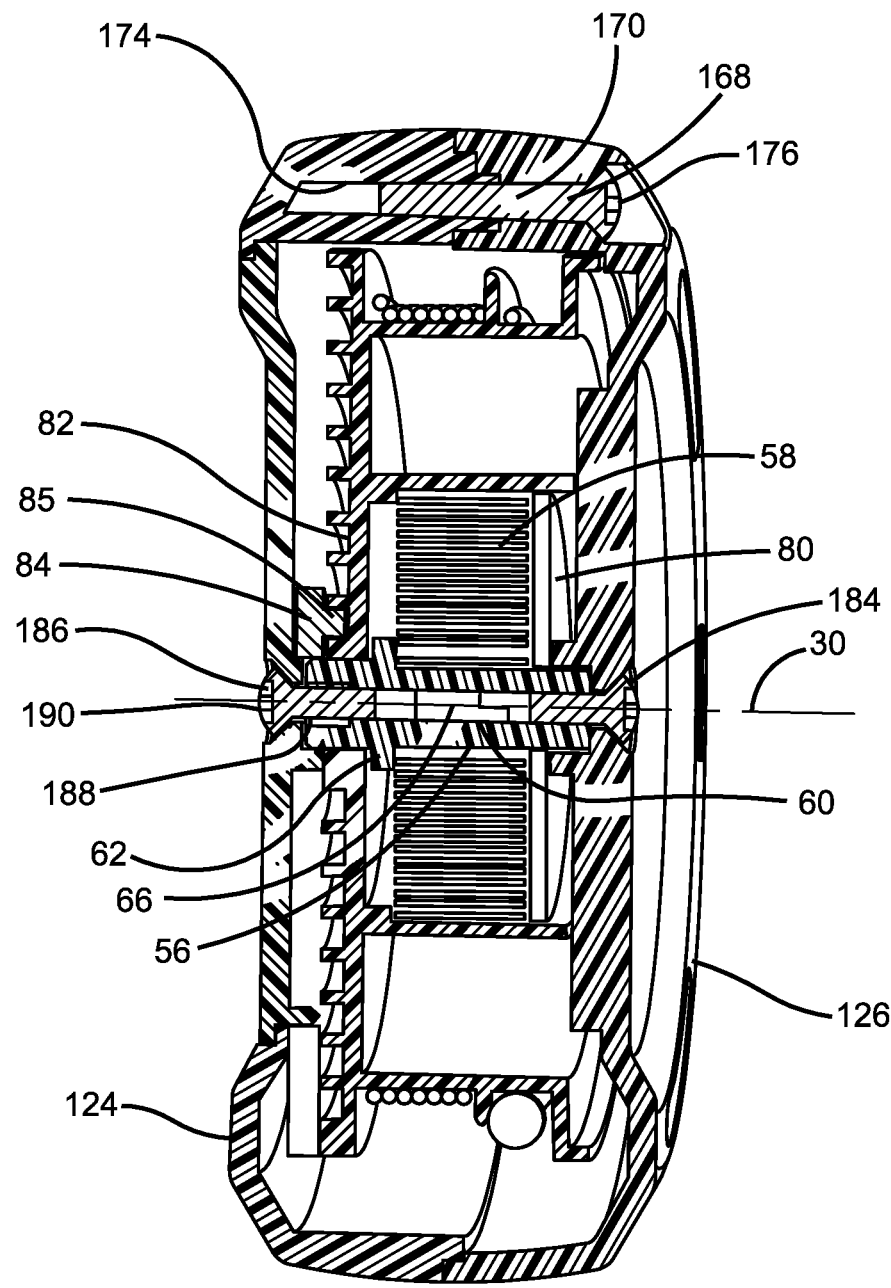
FIG. 6 is a sectional view taken along line 6-6 of FIG. 5.

FIG. 1 shows the apparatus 22 for managing a guidewire 24 (FIG. 2) used to guide a catheter. The apparatus 22 includes a reel 26. The reel 26 comprises a spool 28 that rotates about an axis 30 (FIG. 6). Referring to FIG. 2, the spool 28 is generally made of plastic and includes a cylindrical core 32 and walls 34 on the sides to retain a spool wire 36 and the guidewire 24 wound or coiled around the core 32. The core 32 includes a lane divider wall 38 that separates the core 32 into a spool wire area 40 in which the spool wire 36 may be wound around and a guidewire area 42 (FIG. 1) in which the guidewire 24 may be wound around as seen in FIG. 2. The lane divider wall 38 prevents the guidewire 24 and the spool wire 36 from getting tangled together. The spool wire 36 may be formed of a nylon filament or any other stiff plastic or metallic material. The spool wire 36 has an inner end 44 (FIG. 1) that is inserted into an aperture or divot 46 formed in the spool core 32 at the spool wire area 40 to retain the spool wire 36 to the spool and enable the spool wire 36 to wind around the spool core 40.

Figure 3:
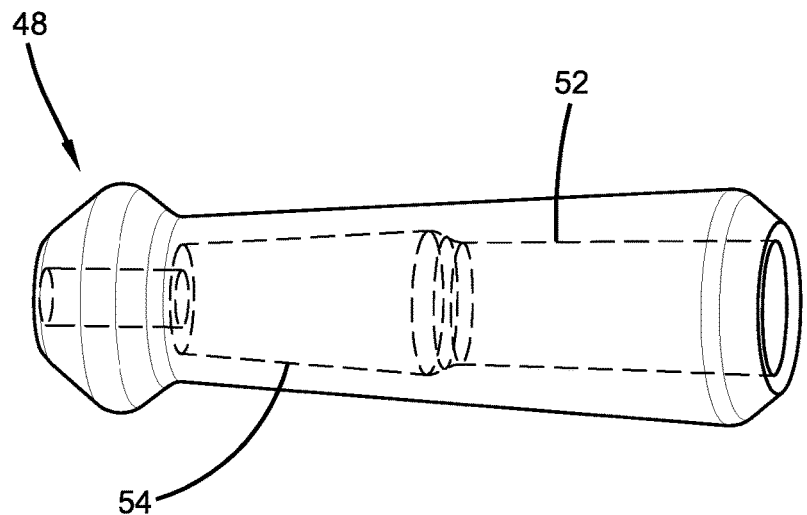
FIG. 3 is a perspective view of wire connector of the apparatus of FIG. 1 with portions in hidden lines.

A wire connector 48 (FIG. 1) is attached to the outer mushroomed tip 50 (FIG. 1) of the spool wire 36. The wire connector 48 couples the guidewire 24 and the spool wire 36 together. In particular as illustrated in FIG. 3, the connector core 52 has beveled inner wall 54 that defines a conical shape opening that increases the friction between the guidewire 24 and mushroomed tip 50 of the spool wire 36 the further the guidewire 24 extends into spool wire 36. The wire connector 48 secures the guidewire to the spool wire 36 by frictional engagement of the inner wall 54 of the connector against the spool wire and the inner wall of the spool wire 36 against the guidewire 24. The wire connector 48 can also be fabricated in other configurations that utilize mechanical (frictional) forces to grip the guidewire 24. The guidewire 24 may be decoupled from the wire connector 48 for utilization of the guidewire 24 in its standard format with other endovascular devices.

Figure 4:
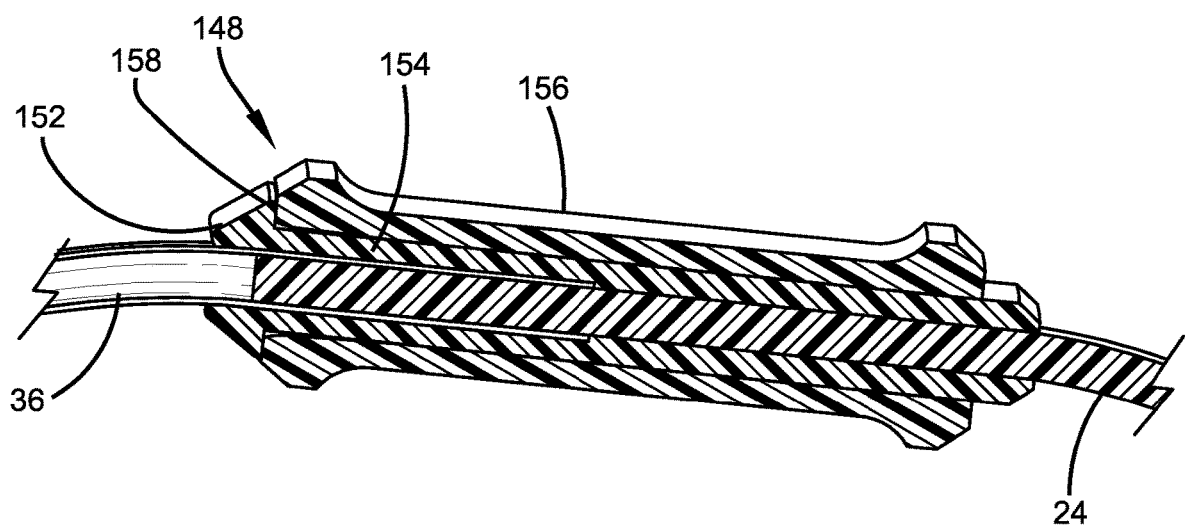
FIG. 4 is a longitudinal sectional view of an alternative wire connector.

FIG. 4 shows an alternative version of the wire connector 148. In this version, the wire connector 148 includes a cylindrical connector core 152 that is received by a sleeve 156. The connector core 152 has a retaining flange 158 on the spool wire 36 end that engages the sleeve 156 to retain the core 152 to the sleeve 156. The core 152 includes a longitudinal bore defined by an inner wall 154 that receives the spool wire 36 and guidewire 24. The end of the spool wire 36 inside the core 152 also receives the end of the guidewire 24. The wire connector 148 secures the guidewire 24 to the spool wire 36 by frictional engagement of the inner wall 154 of the connector core 152 against the spool wire 36 and the inner wall of the spool wire 36 against the guidewire 24.

Figure 7:
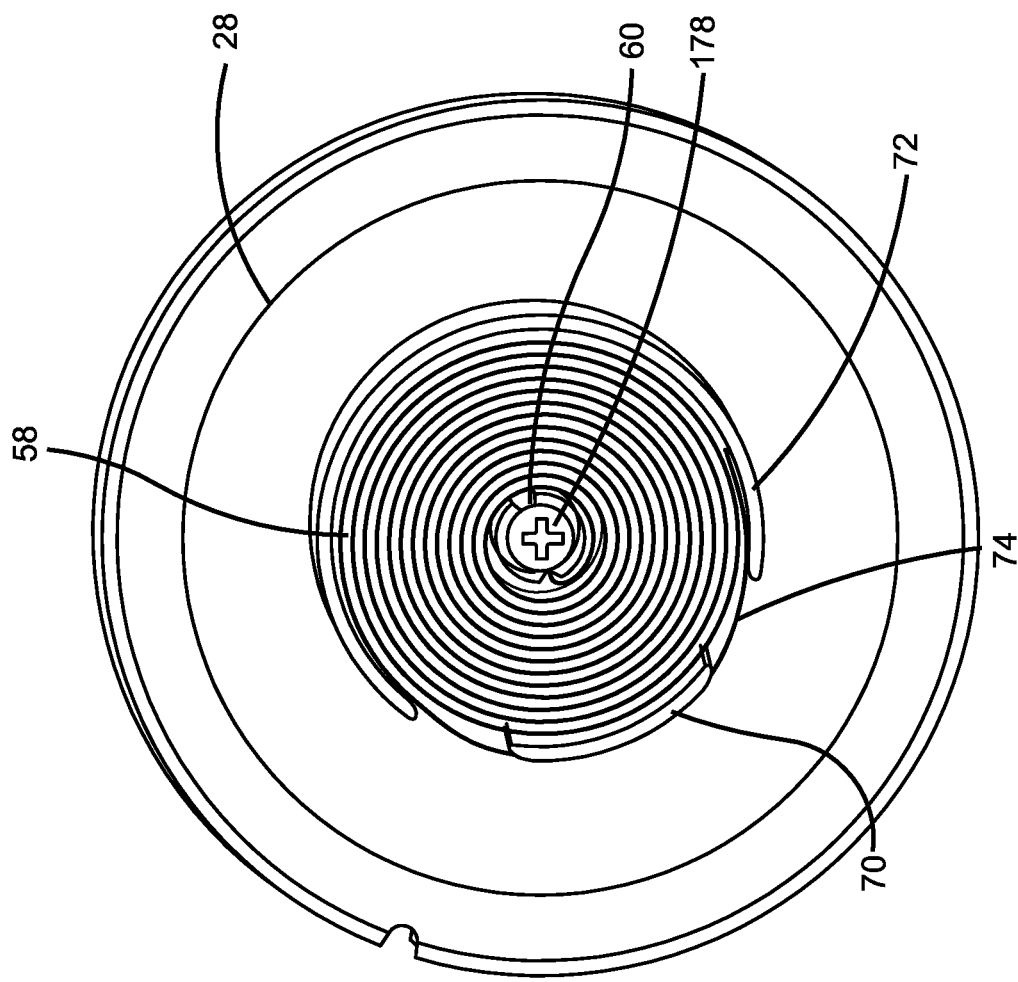
FIG. 7 is a rear and left perspective view of a portion of the apparatus of FIG. 1 depicting the spool, spool spring, axle and related parts.

The spool 28 is rotatably connected to the reel 26 via an axle 56 and spool spring 58. Referring to FIGS. 1, 2, 6, and 7, the axle 56 is hollow and has opposite longitudinal slits 60 and a retaining flange 62. The spool spring 58 is in the form of a spiral torsion spring and has a hub 64 (FIG. 2) and an inner end 66 (FIG. 6) and an outer end 68 (FIG. 1). The axle 56 extends through a longitudinal central bore of the spool 28 and the hub 64 of the spool spring 58 such that the retaining flange 62 abuts against the front side of the spool spring 58 as seen in FIG. 6. The inner end 66 of the spool spring 58 extends through the slits 60 going from the left slit to the right slit to retain the spool spring 58 on the axle 56. The spool 28 includes circumferentially spaced apart arcuate wall portions 70, 72 that retain the spool spring 58 to the spool 28. In particular, as seen in FIGS. 2 and 7, the outer band 74 of the spool spring 58 engages the outer side 76 of the small arcuate wall portion 70 and also engages the inner side 78 of the large arcuate wall portion 74 such that the force of the spool spring 58 urges the spool 28 to rotate the spool 28 in the direction that winds the guidewire 24 and the spool wire 36 around the spool 28. As seen in FIGS. 1 and 6, the axle 56 also receives a spool washer 80. The spool washer 80 is position rearwardly adjacent the rear side of the spool spring 58 and keeps the spool spring 58 in optimal alignment during the guidewire 24 and the spool wire 36 retraction and extraction process. The front side of the spool 28 includes a spiral groove 82 that slidably receives a rear projection 85 of a spool stop 84 as illustrated in FIG. 6.

Figure 8:
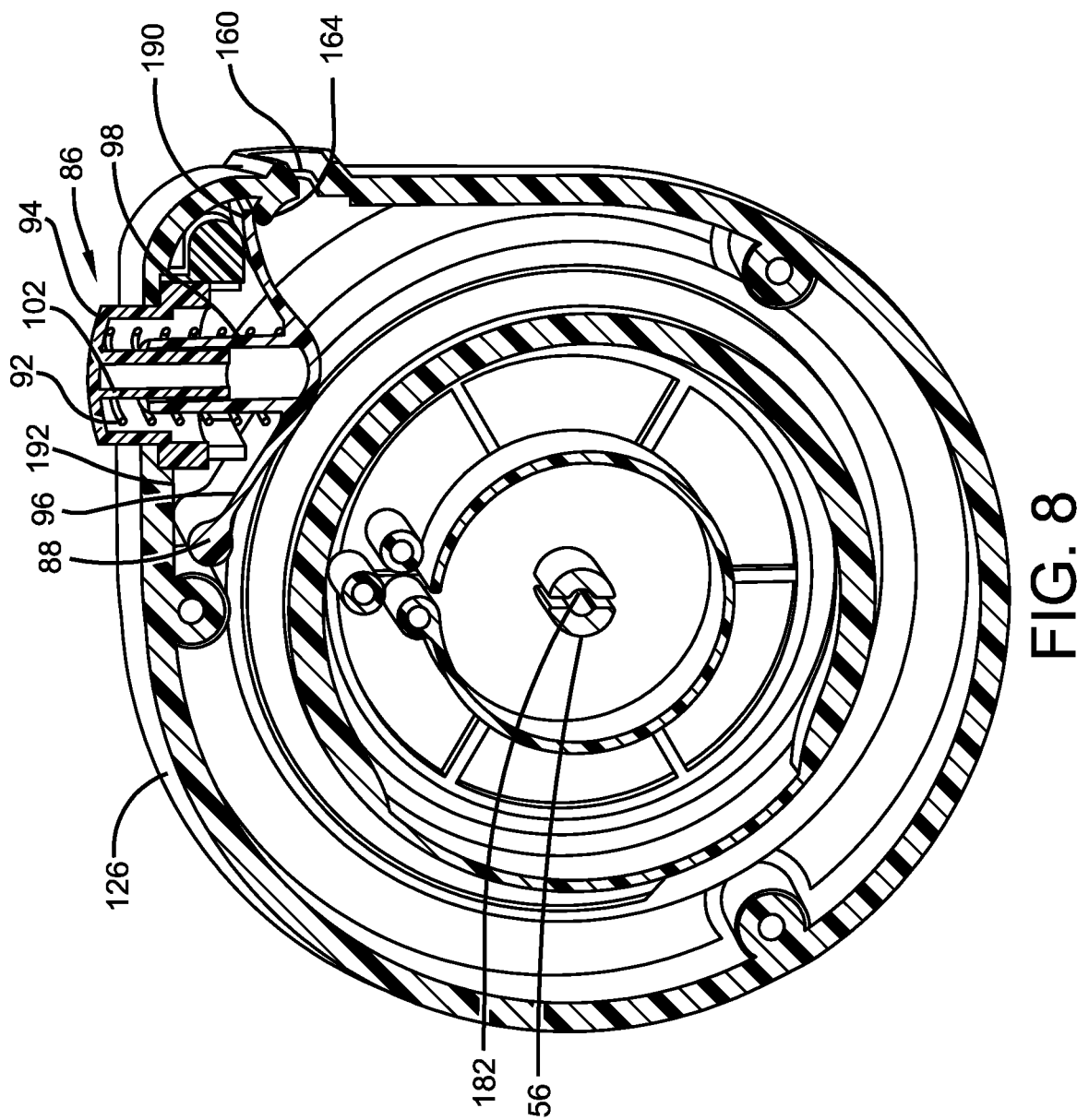
FIG. 8 is a cross sectional view of the apparatus of FIG. 1 taken through the center of the brake button.
Figure 9:
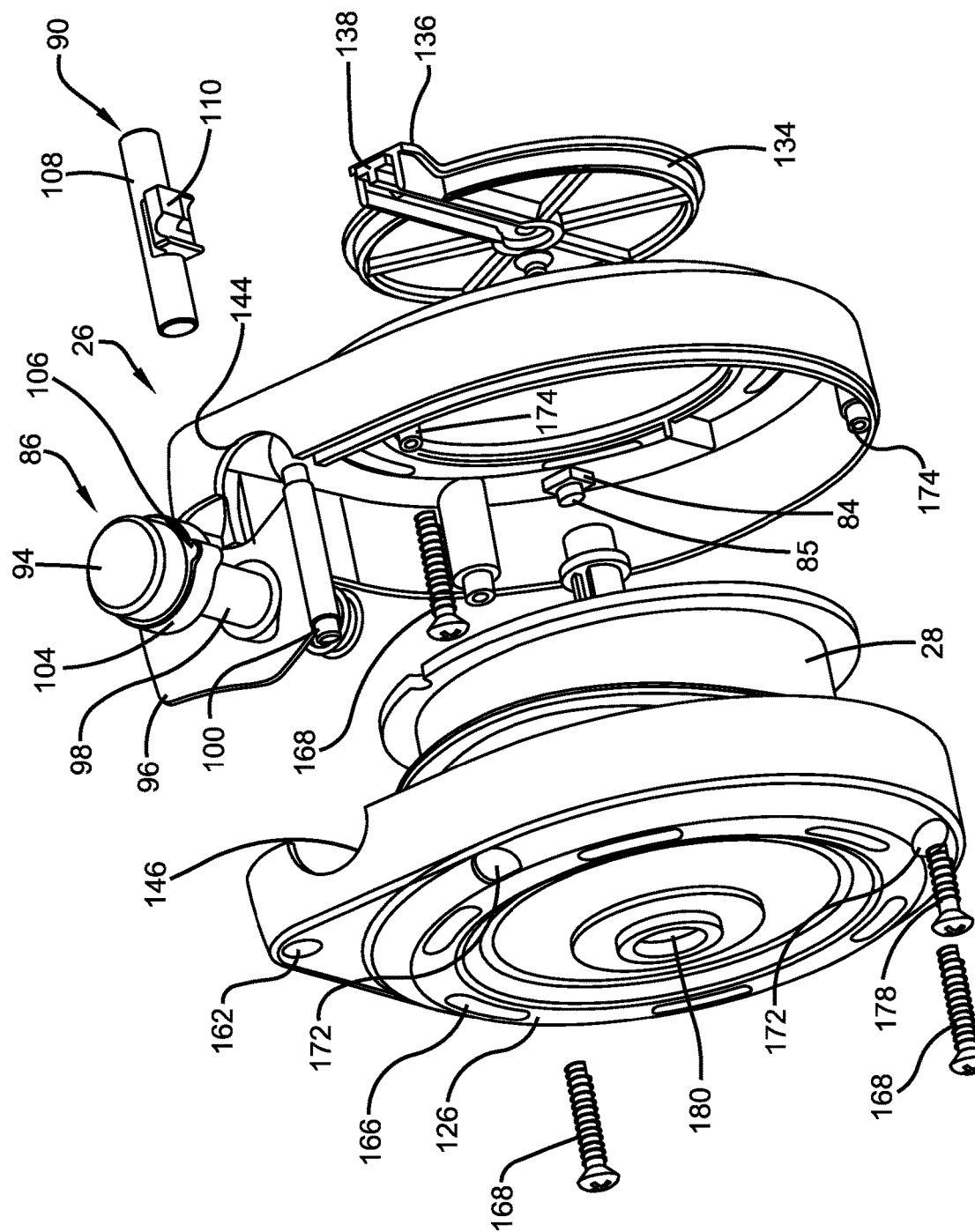
FIG. 9 is an exploded view of the apparatus of FIG. 1 as viewed from the rear and left side.

Referring to FIGS. 1, 8, and 9, the reel 26 includes a brake assembly 86 for stopping and controlling the retraction or extraction of the guidewire 24. In particular, the brake assembly 86 includes a brake 88, a brake lock 90, a spring 92, and a brake push button 94. The brake has a rectangular pad 96 that is u-shaped as view from the front or rear. An upward extending boss 98 is provided on the bight portion of the pad. The brake pad 96 includes an axle 100 on the left end that is rotatably connected to the reel 26. The axle 100 enables the pad to pivot up and down when assembled to the reel. As illustrated in FIG. 8, the brake spring 92 is a coiled spring that receives the boss 98 and may be made by any suitable metallic material. The brake button 94 is oriented vertically and perpendicular to the rotating axis 30 of the spool 28. The brake button 94 includes an inner boss 102 that extends downwardly from the button 94. The inner boss 102 extends into the brake spring 92 and into the boss 98 of the brake pad 96 to slidably secure the brake button 92 to the brake 88. The brake spring 92 biases the brake button 94 upwardly in the unlocked position. The brake button 94 further includes a lower flange 104 that has a nub on the right side that defines a stop member 106 (FIG. 9).

Figure 10:
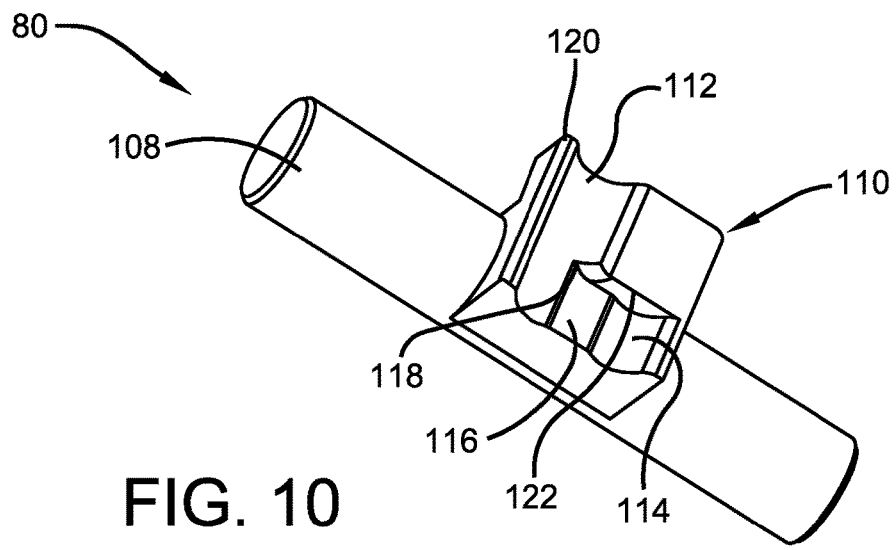
FIG. 10 is a left side perspective view of the brake lock of the apparatus of FIG. 1.
Figure 12:
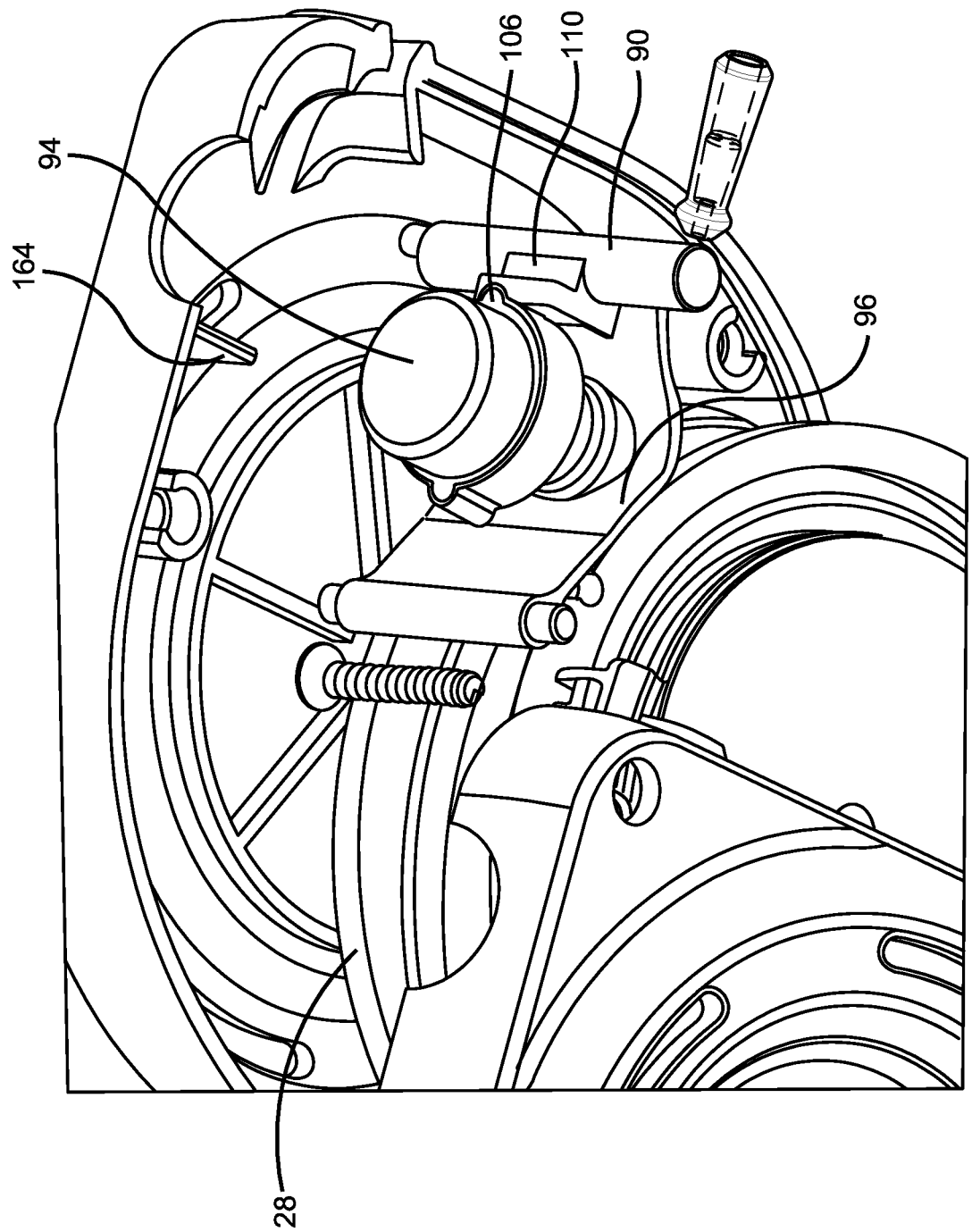
FIG. 12 is a top and front perspective view of a portion of the apparatus of FIG. 1 with portions removed to show the brake assembly in the unlocked position.

The brake lock 90 includes an elongated push rod 108 that is oriented horizontally and parallel to the rotating axis 30 of the spool 28 as depicted in FIG. 9. The brake lock 90 also includes a lock body 110 that is attached to the inner side of the push rod 108 near the center of the push rod 108. As illustrated in FIG. 10, the lock body 110 includes a rear guide grove 112, front groove 114, and intermediate groove 116 located at the left or outer side of the lock body 110. The rear guide groove 112 extends downwardly from the top of the lock body 110. The front and intermediate grooves 114, 116 extend downwardly approximately from the middle of the lock body 110. The intermediate groove 116 is located between the front groove 114 and rear guide groove 112. The intermediate groove 116 includes a beveled upper corner 118 that angles upwardly towards the rear guide groove 112. The front groove 114 and rear guide groove 112 are formed deeper into the lock body 110 than the intermediate groove 116. As illustrated in FIG. 12, the rear guide groove 112 slidably receives the stop member 106 and enables the stop member 106 to slide along the rear guide groove 112 when the brake button 94 moves up and down.

Figure 13:
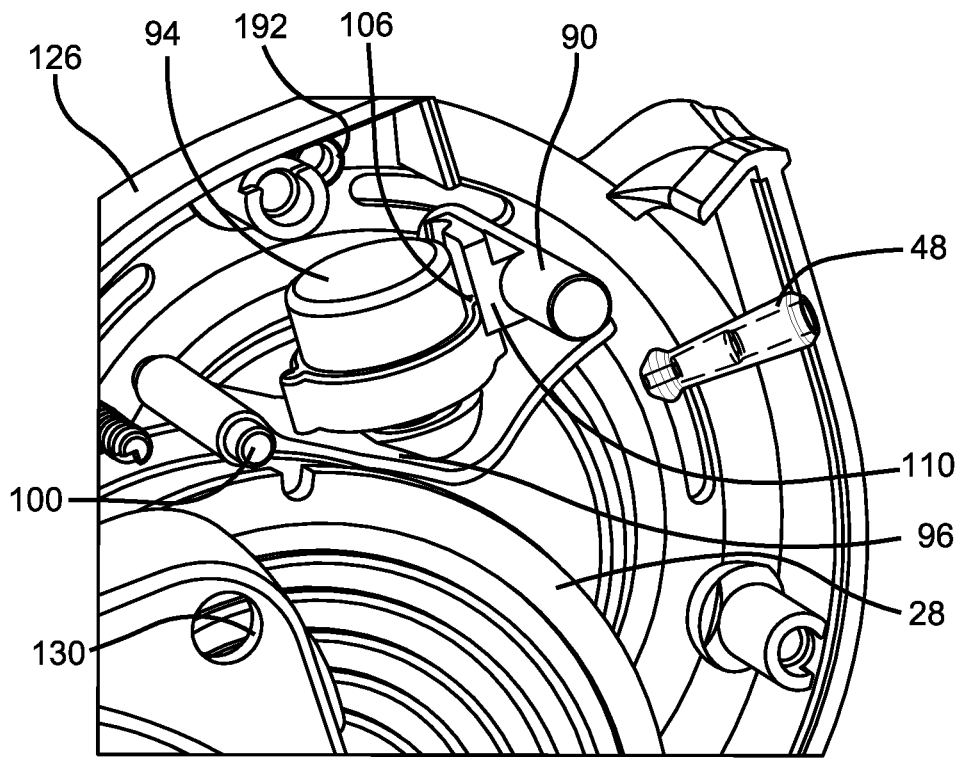
FIG. 13 is a top and front perspective view of a portion of the apparatus of FIG. 1 with portions removed to show the brake assembly in the locked position.

When the brake button 94 is in the rear guide groove 112 and extends above the height of the intermediate and front grooves 116, 114, the opposite longitudinal ends 120 of the rear guide groove 112 prevent the brake lock 90 from being pushed forward or rearward. When the brake button 94 is pushed down until the stop member 106 is below the height of the intermediate and front grooves 116, 114, the brake lock 90 may be pushed rearward until the stop member 106 seats into the front groove 114 as illustrated in FIG. 13. The beveled upper corner 118 of the intermediate groove 116 facilitates the movement of the stop member 106 from the rear guide groove 112 to the intermediate grove 116. The upper ledge 122 defined by the intermediate and front grooves 116, 114 engages the stop member 106 to prevent the brake button 94 from moving upward to an extended position. This enables the brake lock 90 to key in with the brake button 94 so that the brake pad 96 bears against the rear housing 126 to maintain constant friction on the guidewire 24.

Figure 5:
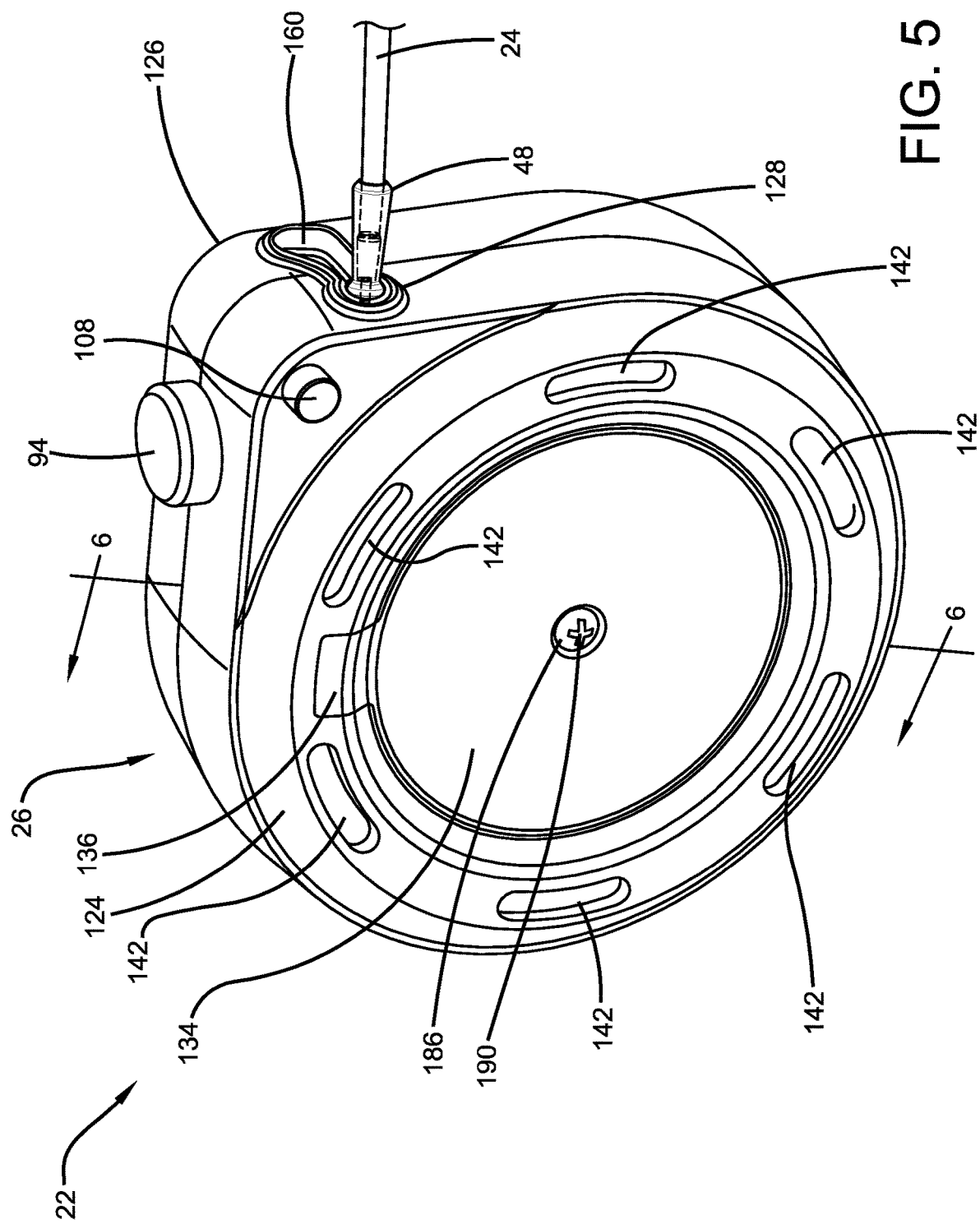
FIG. 5 is a front and right side perspective view of the apparatus of FIG. 1.
Figure 11:
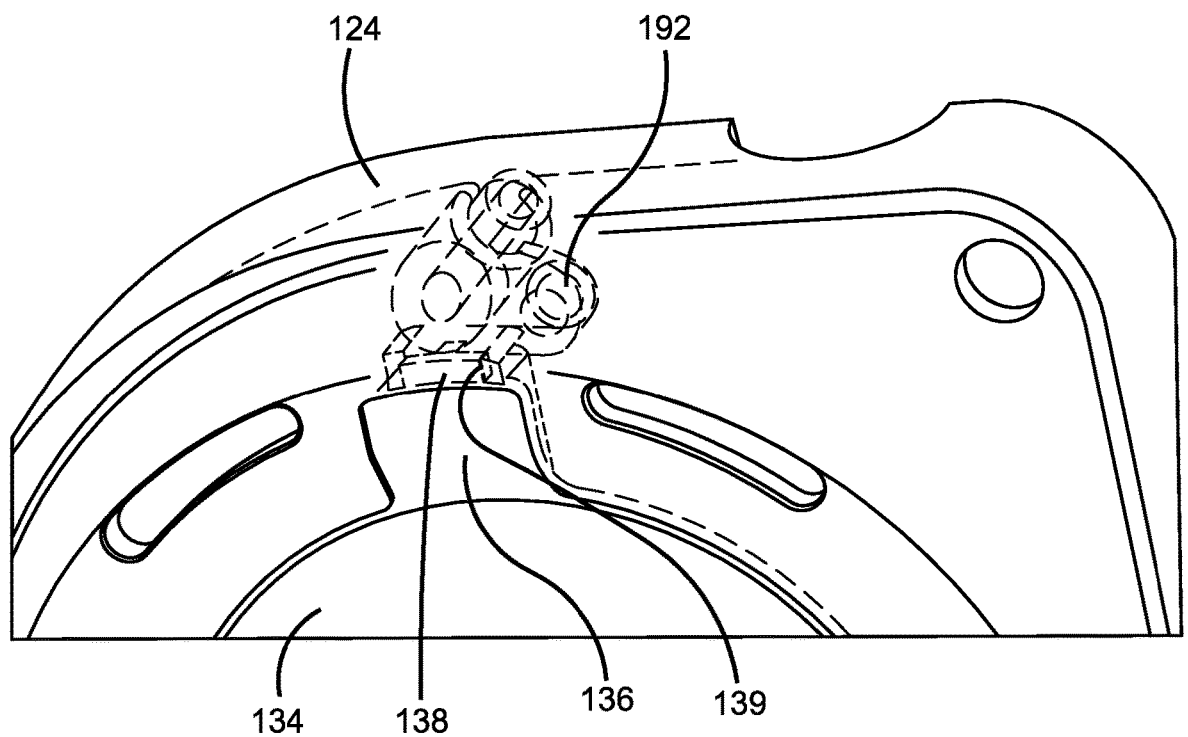
FIG. 11 is a front perspective view of a portion of the apparatus of FIG. 1 depicting the tongue of the housing cap engaging the front housing.
Figure 14:
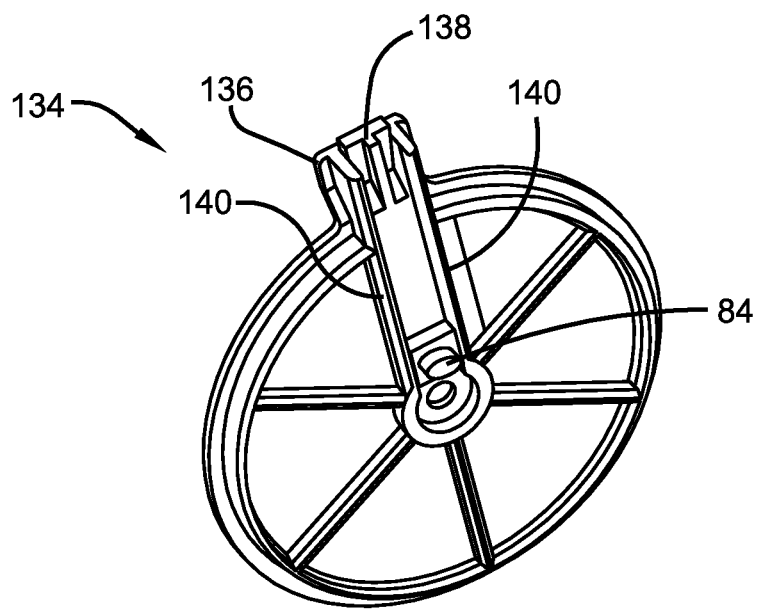
FIG. 14 is a top and rear perspective view of the stool stop inside the housing cap of the apparatus of FIG. 1.

The reel 26 further includes front and rear clam shaped housings 124, 126 as illustrated in FIGS. 1, 5 and 9. The housings may be made of plastic or other suitable material. The front housing 124 includes a small opening 128 on the right side that is sized to receive the guidewire 24 but prevent the wire connector 48 for passing through it as illustrated in FIG. 5. This allows the wire connector 48 to be nested outside the front housing 124 thereby preventing retraction of the spool wire 36 or guidewire 24. The front housing 124 includes a front aperture 130 located on the upper right hand corner in which a front portion of the rod 108 of the brake lock 90 extends through. The front housing 124 includes a central opening 132 on the front side that is covered by a housing cap 134. Specifically, the housing cap 134 includes a tongue 136 that extends radially outwardly from the top of the housing cap 134. The top of the tongue 136 includes a T-shaped projection 138. As illustrated in FIG. 11, when the housing cap 134 is assembled to the front housing 124, the tongue 136 fits into a matching recess 139 formed in the front housing 124, thereby engaging the housing cap 134 to the front housing 124. The housing cap 134 covers and holds the spool stop 84 to the rear side of the spool 28 as illustrated in FIGS. 6 and 14. In particular, the spool stop 84 is position between parallel opposing ribs 140 or pillars formed on the rear side of the housing cap 134 that extend radially as illustrated in FIG. 14. The ribs 140 allow the spool stop to slidably move up and down along the channel defined by the ribs 140 yet constrain lateral movement of the spool stop 84 as the spool stop 84 moves up and down due to rotation of the spiral groove 82 caused by rotation of the spool 28. The spool stop 84 acts as a brake to slow the rotation of the spool 28. This allows for a consistent wire retraction and extraction.

The front housing 124 also includes a series of spaced apart slots or cut-outs 142 (FIG. 5) that circumferentially extend around and surround the housing cap 134 when the cap 134 is installed to the front housing 124. The cut-outs 142 allow fluid to get to the spool 28, thereby keeping the guide-wire lubricated and free of debris. The front housing 124 has a cut-out 144 (FIG. 9) on the top side that cooperates with a similar cut-out 146 (FIG. 9) on the top side of the rear housing 125 to define a top aperture which allows access to push the brake button 94.

The rear housing 126 includes a large opening 160 (FIG. 5) on the right side that is sized to allow the wire connector 48 to pass through it thereby allowing the guidewire 24 to retract and extract. The large opening 160 and small opening 128 merge together such that the guidewire 24 or the spool wire 36 passing through the small opening 128 or large opening 160 may freely move between the large opening 160 and the small opening 128. The rear housing 126 also includes a rear aperture 162 (FIG. 9) located on the upper right hand corner in which a rear portion of the rod 108 of the brake lock 90 extends through. The rear housing 126 further includes an inner step 164 (FIGS. 1 and 8) that is located adjacent the upper end of the large opening 160. The rear housing 126 further includes a series of spaced apart slots or cut-outs 166 (FIG. 9) that circumferentially extend around and surround the rear housing 126. The cut-outs 166 allow fluid to get to the spool 28, thereby keeping the guidewire 24 lubricated and free of debris.

Referring to FIGS. 1, 2, 6 and 9, three housing screws 168 secure the rear housing 126 to the front housing 124. In particular, each shaft 170 of the housing screw 168 extends into an aperture 172 of the rear housing 126 and is screwed into a respective boss 174 (FIGS. 6 and 9) on the rear side of the front housing 124, and the head 176 of each housing screw 168 engages the rear side of the front housing 124 to thus secure the rear housing 126 to the front housing 124 as seen in FIG. 6.

A rear axle screw 178 secures the rear housing 126 to the axle 56. In particular, a shaft of the rear axle screw 178 extends into a central aperture 180 (FIG. 9) of the rear housing 126 and is screwed into a rear portion of the bore 182 (FIG. 8) of the axle 56, and the head 184 of the rear axle screw 178 engages the rear side of the rear housing 126 to thus secure the rear housing 126 to the axle 56. A front axle screw 186 secures the housing cap 134 to the axle 56. In particular, a shaft 188 of the front axle screw 186 extends into the central aperture 133 (FIG. 1) of the housing cap 134 and is screwed into a front portion of the bore 182 of the axle 56, and the head 190 of the front axle screw 186 engages the front side of the front housing 124 to thus secure the front housing 124 to the axle 56.

When the reel 26 is assembled, the free end 190 opposite the axle 100 of the brake pad 96 engages the inner step 164 (FIG. 8). As illustrated in FIGS. 8 and 12, the brake pad 96 may lightly contact the walls of the spool 28 or be slightly spaced above the walls to allow the spool to rotate relative to the front and rear housings 124, 126 about the axis 30 of rotation when the brake button 94 is not depressed. Also, the ends of the brake pad axle 100 are rotatably received by respective bearings 192 (FIGS. 8, 11 and 13) of the front and rear housings 124, 126. In operation, with the brake assembly 86 in the unlocked position as shown in FIG. 12, a user may extract the guidewire 24 for use by grasping the guidewire 24 at a location outside of the reel 26 and pulling the guidewire 24 with sufficient force to overcome the force of the spool spring 58. The user may extract the guidewire 24 until the wire connector 48 passes through the large opening 160 and out the reel 26. Upon the wire connector 48 passing through the large opening 160 and out the reel 26, the wire connector 48 may be moved over to the smaller opening 128 so that the wire connector 48 engages (or nests) in the smaller trough or opening 128 of the front housing 124 as illustrated in FIG. 5. This smaller trough or smaller opening 128 prevents retraction of the wire connector 48 and guidewire 24 into the spool 28.

To stop retraction or extraction movement of the guidewire 24 at a certain length, a user may depress the brake button 94 with sufficient force to pivot (or disort) the brake pad 96 and increase the frictional force on the spool 28 (or reel). Disorting the brake pad 96 and increasing the frictional force on the spool 28 increases the drag on the guidewire 24 and spool 28 respectively, and depending on the amount of force applied, the retraction or extraction process is either decreased or stopped. To lock the brake 88 in this locked position without having to keep the brake button 94 depressed, a user pushes the push rod 108 of the brake lock 90 rearward until the stop member 106 seats into the front groove 114 and the ledge 122 engages the stop member 106 preventing the brake button 94 and brake pad 96 from moving upward to in turn to keep the guidewire 24 and spool motion clamped. FIG. 13 illustrates the brake 88 locked in this locked position. To release the brake lock 88, the user pushes the rear portion of the push rod 108 forwardly until the rear guide groove 118 slidably receives the stop member 106. In this position, the force of the brake spring 92 moves the brake button 94 upwardly, which in turn causes the brake pad 96 to pivot upwardly and release the clamping force on the guidewire 24 and spool 28. The guidewire 24 is then free to retract or be extracted.

Figure 15:
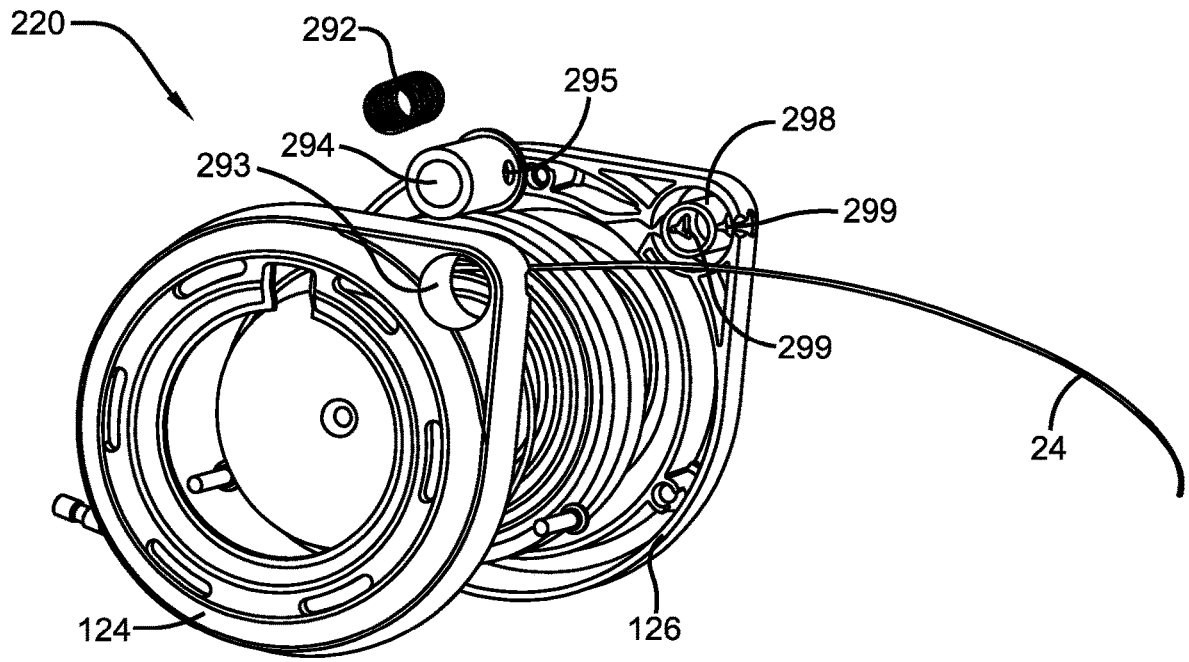
FIG. 15 is an exploded view an exploded view of the apparatus for managing a guidewire as viewed from the front and right side according to another embodiment of the present invention.
Figure 16:
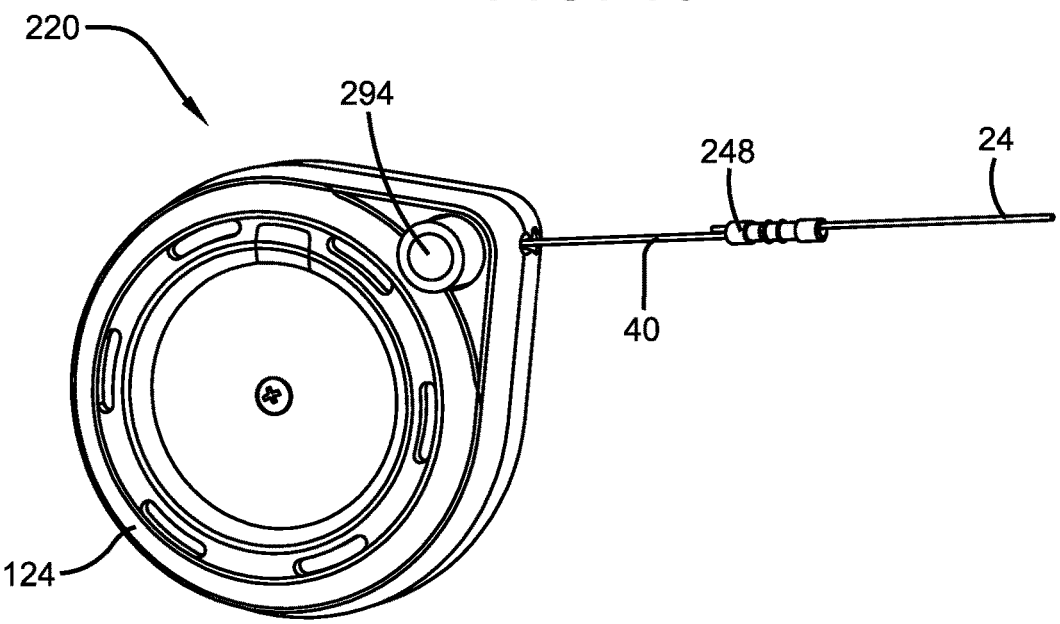
FIG. 16 is a front and right side perspective view of the apparatus of FIG. 15.

FIGS. 15 and 16 show another embodiment of the present invention. The embodiment of FIGS. 15 and 16 are similar to the embodiment illustrated in FIGS. 1 to 14 except for the different subject matter described below. In this embodiment, the apparatus 220 has the brake button 294 and brake spring 292 oriented horizontally and parallel to the rotating axis of the spool 28. The brake button 294 extends through a lateral aperture 293 of the front housing 124. The brake button 294 is hollow with a pair of opposite lateral apertures 295. The rear housing 126 includes a boss 298 that extends forwardly from the front side of the rear housing 126. The boss 298 includes a pair of apertures 299 located on opposite sides. The brake spring 292 receives the boss 298 and extends into the interior of the brake button 294. The guidewire 24 is inserted through the lateral apertures. When the brake button 294 is extended the apertures 295 of the brake button 294 are not aligned with the apertures 299 of the boss 298 and the guidewire 24 is clamped by the rear housing 126 and brake button 294 in the locked position to prevent the guidewire 24 from retracting and extracting. When the brake button 294 is pushed rearwardly until the apertures 295, 299 are aligned together, the guidewire 24 is not clamped by the rear housing 126 and brake button 294, such that the guidewire 24 may be free to retract or extract. The brake lock 90 may or may not be provided in this embodiment. Also, the wire connector 248 may have first and second longitudinal bores in that securely receive the guidewire 24 and the spool wire 36, respectively, for frictional engagement therein.

Figure 17:
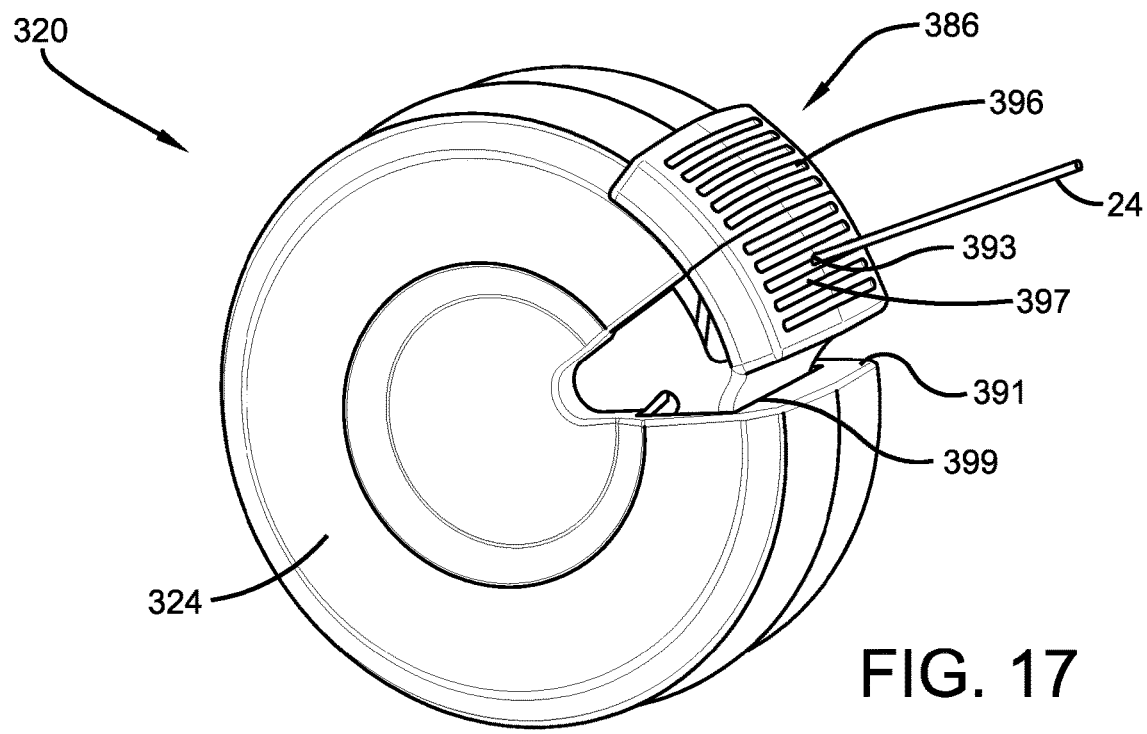
FIG. 17 is a front and right side perspective view of the apparatus for managing a guidewire according to another embodiment of the present invention.
Figure 18:
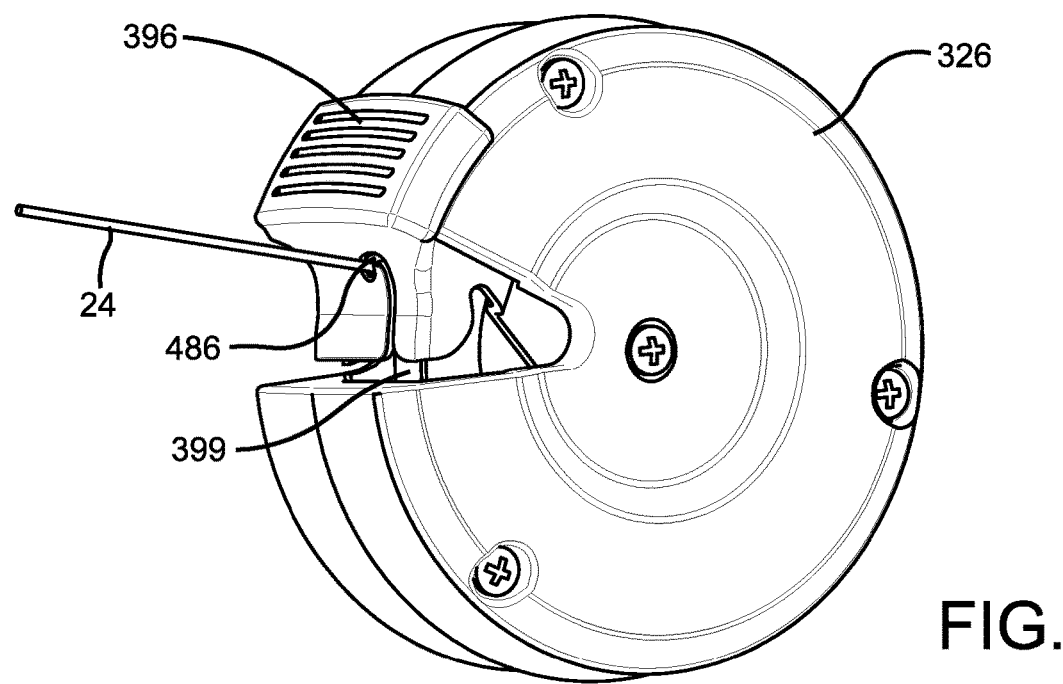
FIG. 18 is a rear and right side perspective view of the apparatus of FIG. 17.

FIGS. 17 and 18 show another embodiment of the present invention. The embodiment of FIGS. 17 and 18 are similar to the embodiment illustrated in FIGS. 1 to 14 except for the different subject matter described below. In this embodiment, the apparatus 320 include a brake 386 that includes a brake pad 396 and a lock tab 397 located adjacent the brake pad 396. The brake pad 396 and the lock tab 397 are pivotally connected to the axle. The brake pad 396 and lock tab 397 are positioned in a cut-out sector 399 of the front and rear housings 324, 326 with the lock tab 397 spaced from the edge 391 of the housing that defines a radius end of the cut-out sector 399. The brake pad 396 has a slot 395 (FIG. 18) that receives the guidewire 24. The slot is covered by the lock tab 397. The lock tab 397 has an aperture 393 that receives the guidewire 24. Movement of the lock tab 397 in the direction away from the brake pad 386 until the lock tab 397 reaches the edge 391 of the housings locks the guidewire 24 in that position to prevent retraction and extraction of the guidewire 24.

Figure 19:
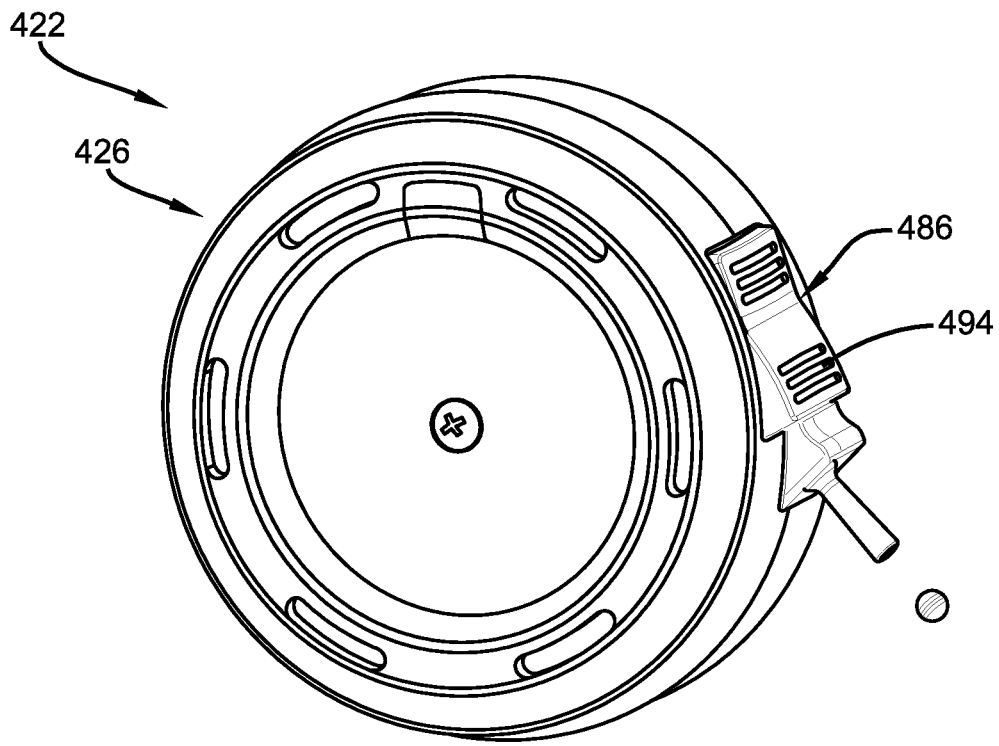
FIG. 19 is a front and right side perspective view of the apparatus for managing a guidewire according to another embodiment of the present invention.
Figure 20:
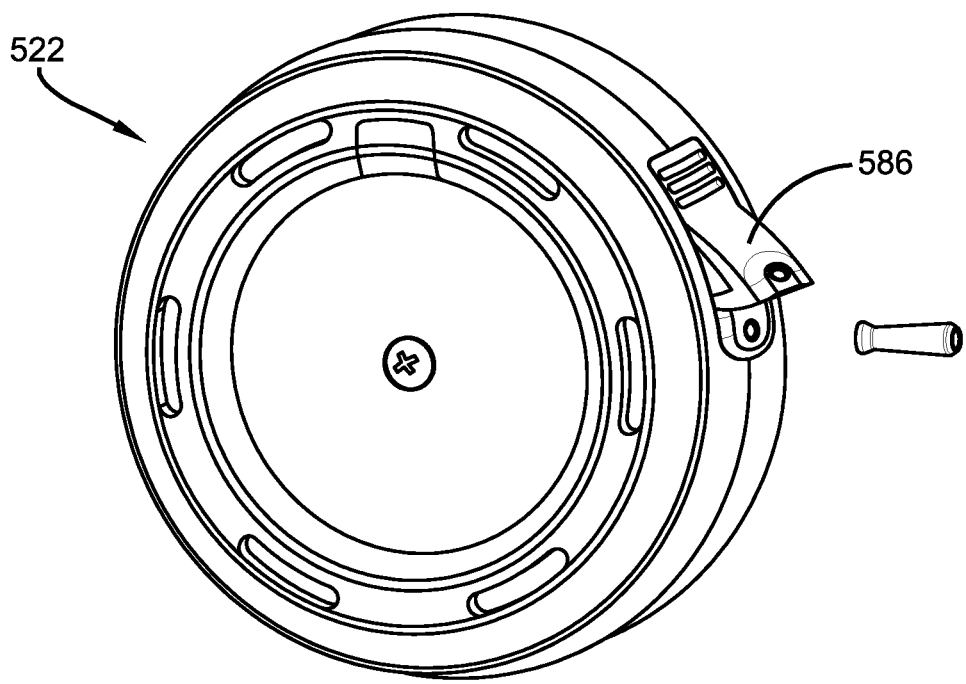
FIG. 20 is a front and right side perspective view of the apparatus for managing a guidewire according to another embodiment of the present invention.

FIG. 19 shows another embodiment of the present invention. The embodiment of FIG. 19 is similar to the embodiment illustrated in FIGS. 1 to 14 except for the different subject matter described below. In this embodiment, the apparatus 422 includes a brake 486 in the form a rocker switch. The rocker switch 486 is pivotally connected to the reel 426 and located adjacent the hole in the housing that receives the guidewire 24. Pressing on the end 494 of the rocker switch 486 adjacent the hole clamps the guidewire 24 to the reel 426 and prevents retraction and extraction of the guidewire 24. FIG. 20 shows another embodiment of the present invention in which the apparatus 522 has a different variation of the rocker switch 586.

Additional embodiments or modification to the present invention may include the following. An assortment of multiple reciprocating hooks may be provided on the housings of the apparatus to provide the additional ability of constraining a portion of a longer guidewire that remains outside the apparatus after maximal retraction by the spool spring.

A gear system may be provided that adjusts the rotational ratio of the spool and the spool-stop system when using longer wires such as, for example, wires that are greater than 5 feet. The gear system may be designed for ten foot and fifteen foot long guidewires such that it becomes compatible with the spool stop system designed for the five foot guidewire. The gear system rations are 2:1 or 3:1, wherein two (or three) rotations of the spool result in one rotation of the spool stop on the spiral groove.

The present invention makes the storage, cleansing, and access of guidewires during medical and surgical procedures more efficient. The apparatus for managing a guidewire has a small foot print so that a much smaller side table may be utilized, thereby reducing space requirements for medical procedures that require a guidewire. The apparatus for managing a guidewire also reduces guidewire exchange time. This reduction in procedural time is associated with a reduction in radiation exposure time which safety-wise is advantageous for both intraoperative personnel and the patient. A reduction in procedural time is associated with a reduction in sedation/anesthesia requirements.

Also, the apparatus for managing a guidewire constrains the guidewire in a strong casing to prevent the guidewire from uncoiling, thereby reducing wire contamination and damage. A reduction in the risk of wire contamination reduces the risk of foreign-body related infections. The apparatus for managing a guidewire enable the resolution of wire migration (externally or internally) by using the brake lock, thereby maintaining the desired wire-tip location for critical portions of complex procedures. The reduction in space and time also lowers the cost for medical procedures that require a guidewire.

Although various embodiments of the disclosed apparatus and method for managing a guidewire have been shown and described, modifications may occur to those skilled in the art upon reading the specification. The present application includes such modifications and is limited only by the scope of the claims.

What is claimed is:

1. An apparatus for storing and directing a guidewire used to guide an instrument comprising:
    a spool, wherein the spool receives the guidewire, wherein rotation of the spool in a first direction retracts the guidewire around the spool;
    a housing, wherein the housing houses the spool, wherein the housing includes a cap, wherein the cap is removably attached to the housing; and
    a spool stop member, wherein the spool stop member is provided between the cap and the spool, wherein the spool stop member is configured to brake the spool during rotation of the spool, wherein the spool has a groove, wherein the groove slidably receives the spool stop member, wherein the spool stop member is configured to slide along the groove during rotation of the spool, wherein the groove is spiral shaped, wherein the housing includes a channel, wherein the channel slidably receives the spool stop member, wherein the spool stop member is configured to slide along the channel during rotation of the spool.

2. The apparatus of claim 1, wherein the housing comprises at least one slot, wherein the slot is configured to allow fluid to pass therethrough for lubricating the guidewire on the spool.

3. The apparatus of claim 1 further comprising:
    a spool wire, wherein the spool receives the spool wire, wherein rotation of the spool in a first direction retracts the spool wire around the spool;
    a wire connector, wherein the wire connector operatively couples the spool wire and the guidewire together, wherein the housing comprises first and second apertures, wherein the first aperture is sized to prevent the wire connector from passing through the first aperture but allow the guidewire and the spool wire to pass through the first aperture, wherein the second aperture is sized to allow the wire connector and the guidewire and the spool wire to pass through the second aperture, wherein the first and second apertures merge together such that the guidewire and the spool wire may move between the first and second apertures.

4. The apparatus of claim 3 further comprising:
    a brake, wherein the brake may be placed in a first position in which the brake does not prevent the spool from rotating in the first direction, wherein brake may be placed in a second position in which the brake engages the spool to prevent the spool from rotating in the first direction;
    a brake actuator operatively connected to the brake, wherein actuation of the brake actuator causes the brake to move from the first position to the second position; and
    a brake lock, wherein the brake lock is operatively connected to the brake, wherein the brake lock is configured to lock the brake in the second position to prevent the spool from retracting the guidewire without continue actuation of the brake actuator.

5. The apparatus of claim 4, wherein the brake actuator comprises a push button, a biasing member operatively connected to the push button, wherein the biasing member biases the push button in an extended position, wherein the brake is in the first position when the push button is in the extended position, wherein depressing the push button to a retracted position causes the brake to move from the first position to the second position, wherein the brake lock is configured to lock the push button in the retracted position, wherein the brake lock comprises a push rod and a brake body, wherein the brake body has a first guide groove and a second guide groove, wherein the push button includes a push button stop member, wherein the push rod may be moved between an unlocked position and a locked position, wherein the first guide groove is configured to slidably receive the push button stop member and enable the push button stop member to slide along the first guide groove to allow the push button to move between the retracted and extended positions when the push rod is in the unlocked position, wherein the second guide groove is configured to receive the push button stop member and prevent the push button from moving between the retracted and extended positions when the push rod is in the locked position.

6. The apparatus of claim 1 further comprising:
    a brake, wherein the brake may be placed in a first position in which the brake does not prevent the spool from rotating in the first direction, wherein brake may be placed in a second position in which the brake engages the spool to prevent the spool from rotating in the first direction;
a brake actuator operatively connected to the brake, wherein actuation of the brake actuator causes the brake to move from the first position to a second position; and
a brake lock, wherein the brake lock is operatively connected to the brake, wherein the brake lock is configured to lock the brake in the second position to prevent the spool from retracting the guidewire without continue actuation of the brake actuator.

7. An apparatus for storing and directing a guidewire used to guide an instrument comprising:
a spool wire;
a spool, wherein the spool receives the guidewire and the spool wire, wherein rotation of the spool in a first direction retracts the guidewire and the spool wire around the spool;
a wire connector, wherein the wire connector operatively couples the spool wire and the guidewire together; and
a housing, wherein the housing houses the spool, wherein the housing comprises first and second apertures, wherein the first aperture is sized to prevent the wire connector from passing through the first aperture but allow the guidewire and the spool wire to pass through the first aperture, wherein the second aperture is sized to allow the wire connector and the guidewire and the spool wire to pass through the second aperture, wherein the first and second apertures merge together such that the guidewire and the spool wire may move between the first and second apertures.

8. The apparatus of claim 7, wherein the spool comprises a core and a dividing wall, wherein the dividing wall is attached to the core and divides the core into a spool wire area and a guidewire area, wherein the spool wire area is configured for receiving the spool wire, wherein the guidewire area is configured for receiving the guidewire.

9. The apparatus of claim 7 further comprising:
a brake, wherein the brake may be placed in a first position in which the brake does not prevent the spool from rotating in the first direction, wherein brake may be placed in a second position in which the brake engages the spool to prevent the spool from rotating in the first direction;
a brake actuator operatively connected to the brake, wherein actuation of the brake actuator causes the brake to move from the first position to the second position; and
a brake lock, wherein the brake lock is operatively connected to the brake, wherein the brake lock is configured to lock the brake in the second position to prevent the spool from retracting the guidewire without continue actuation of the brake actuator.

10. The apparatus of claim 9, wherein the brake actuator comprises a push button, a biasing member operatively connected to the push button, wherein the biasing member biases the push button in an extended position, wherein the brake is in the first position when the push button is in the extended position, wherein depressing the push button to a retracted position causes the brake to move from the first position to the second position, wherein the brake lock is configured to lock the push button in the retracted position.

11. The apparatus of claim 10, wherein the brake lock comprises a push rod and a brake body, wherein the brake body has a first guide groove and a second guide groove, wherein the push button includes a push button stop member, wherein the push rod may be moved between an unlocked position and a locked position, wherein the first guide groove is configured to slidably receive the push button stop member and enable the push button stop member to slide along the first guide groove to allow the push button to move between the retracted and extended positions when the push rod is in the unlocked position, wherein the second guide groove is configured to receive the push button stop member and prevent the push button from moving between the retracted and extended positions when the push rod is in the locked position.

12. The apparatus of claim 7, wherein the housing comprises at least one slot, wherein the slot is configured to allow fluid to pass therethrough for lubricating the guidewire on the spool.

13. An apparatus for storing and directing a guidewire used to guide an instrument comprising:
a spool, wherein the spool receives the guidewire, wherein rotation of the spool in a first direction retracts the guidewire around the spool;
a brake, wherein the brake may be placed in a first position in which the brake does not prevent the spool from rotating in the first direction, wherein brake may be placed in a second position in which the brake engages the spool to prevent the spool from rotating in the first direction;
a brake actuator operatively connected to the brake, wherein actuation of the brake actuator causes the brake to move from the first position to a second position; and
a brake lock, wherein the brake lock is operatively connected to the brake, wherein the brake lock is configured to lock the brake in the second position to prevent the spool from retracting the guidewire without continue actuation of the brake actuator;
a spool wire, wherein the spool receives the spool wire, wherein rotation of the spool in a first direction retracts the spool wire around the spool; and
a wire connector, wherein the wire connector operatively couples the spool wire and the guidewire together, wherein the spool comprises a core and a dividing wall, wherein the dividing wall is attached to the core and divides the core into a spool wire area and a guidewire area, wherein the spool wire area is configured for receiving the spool wire, wherein the guidewire area is configured for receiving the guidewire.

14. The apparatus of claim 13, wherein the brake actuator comprises a push button, a biasing member operatively connected to the push button, wherein the biasing member biases the push button in an extended position, wherein the brake is in the first position when the push button is in the extended position, wherein depressing the push button to a retracted position causes the brake to move from the first position to the second position, wherein the brake lock is configured to lock the push button in the retracted position.

15. The apparatus of claim 13 further comprising:
a housing, wherein the housing houses the spool, wherein the housing includes a cap, wherein the cap is removably attached to the housing; and
a spool stop member, wherein the spool stop member is provided between the cap and the spool, wherein the spool stop member is configured to brake the spool during rotation of the spool, wherein the spool has a groove, wherein the groove slidably receives the spool stop member, wherein the spool stop member is configured to slide along the groove during rotation of the spool, wherein the groove is spiral shaped, wherein the housing includes a channel, wherein the channel slidably receives the spool stop member, wherein the spool stop member is configured to slide along the channel during rotation of the spool.

16. The apparatus of claim 13 further comprising a housing, wherein the housing houses the spool, wherein the housing comprises at least one slot, wherein the slot is configured to allow fluid to pass therethrough for lubricating the guidewire on the spool.

17. An apparatus for storing and directing a guidewire used to guide an instrument comprising:
a spool, wherein the spool receives the guidewire, wherein rotation of the spool in a first direction retracts the guidewire around the spool;
a brake, wherein the brake may be placed in a first position in which the brake does not prevent the spool from rotating in the first direction, wherein brake may be placed in a second position in which the brake engages the spool to prevent the spool from rotating in the first direction;
a brake actuator operatively connected to the brake, wherein actuation of the brake actuator causes the brake to move from the first position to a second position; and
a brake lock, wherein the brake lock is operatively connected to the brake, wherein the brake lock is configured to lock the brake in the second position to prevent the spool from retracting the guidewire without continue actuation of the brake actuator, wherein the brake actuator comprises a push button, a biasing member operatively connected to the push button, wherein the biasing member biases the push button in an extended position, wherein the brake is in the first position when the push button is in the extended position, wherein depressing the push button to a retracted position causes the brake to move from the first position to the second position, wherein the brake lock is configured to lock the push button in the retracted position, wherein the brake lock comprises a push rod and a brake body, wherein the brake body has a first guide groove and a second guide groove, wherein the push button includes a push button stop member, wherein the push rod may be moved between an unlocked position and a locked position, wherein the first guide groove is configured to slidably receive the push button stop member and enable the push button stop member to slide along the first guide groove to allow the push button to move between the retracted and extended positions when the push rod is in the unlocked position, wherein the second guide groove is configured to receive the push button stop member and prevent the push button from moving between the retracted and extended positions when the push rod is in the locked position.

* * * * *